(12) United States Patent
Inoue et al.

(10) Patent No.: US 7,476,758 B2
(45) Date of Patent: Jan. 13, 2009

(54) PROCESS FOR PREPARING A PHENYLALANINE DERIVATIVE AND INTERMEDIATES THEREOF

(75) Inventors: Isao Inoue, Toyonaka (JP); Toru Kuroda, Ashiya (JP); Ryuzo Yoshioka, Takatsuki (JP)

(73) Assignee: Mitsubishi Tanbe Pharma Corporation, Osaka (JP)

( * ) Notice: Subject to any disclaimer, the term of this patent is extended or adjusted under 35 U.S.C. 154(b) by 535 days.

(21) Appl. No.: 10/505,723

(22) PCT Filed: Feb. 27, 2003

(86) PCT No.: PCT/JP03/02181

§ 371 (c)(1), (2), (4) Date: Aug. 26, 2004

(87) PCT Pub. No.: WO03/072536

PCT Pub. Date: Sep. 4, 2003

(65) Prior Publication Data

US 2005/0165107 A1 Jul. 28, 2005

(30) Foreign Application Priority Data

Feb. 28, 2002 (JP) ............................. 2002-052605

(51) Int. Cl.
C07C 229/00 (2006.01)
A61K 31/195 (2006.01)
(52) U.S. Cl. ...................................... 562/450; 514/563
(58) Field of Classification Search ................. 514/563; 562/450
See application file for complete search history.

(56) References Cited

U.S. PATENT DOCUMENTS

| | | | |
|---|---|---|---|
| 5,162,311 A | 11/1992 | Herrling et al. | |
| 5,294,632 A | 3/1994 | Erion et al. | |
| 5,455,260 A | 10/1995 | Groneberg et al. | |
| 5,506,244 A | 4/1996 | Fink | |
| 5,703,106 A | 12/1997 | Fruh et al. | |
| 5,780,498 A | 7/1998 | Saika | |
| 5,968,980 A | 10/1999 | Kawashima et al. | |
| 5,976,858 A | 11/1999 | Palmer et al. | |
| 5,977,075 A | 11/1999 | Ksander et al. | |
| 6,069,163 A | 5/2000 | Delaszlo | |
| 6,090,841 A | 7/2000 | Chang et al. | |
| 6,093,696 A | 7/2000 | Head et al. | |
| 6,127,341 A | 10/2000 | Hansen et al. | |
| 6,136,842 A | 10/2000 | Deprez et al. | |
| 6,191,171 B1 | 2/2001 | Delaszlo | |
| 6,197,794 B1 | 3/2001 | Head et al. | |
| 6,221,888 B1 | 4/2001 | Durette et al. | |
| 6,229,011 B1 | 5/2001 | Chen et al. | |
| 6,271,252 B1 | 8/2001 | Chang et al. | |
| 6,291,511 B1 | 9/2001 | Durette et al. | |
| 6,329,372 B1 | 12/2001 | Head et al. | |
| 6,353,099 B1 | 3/2002 | DeLaszlo et al. | |
| 6,362,204 B1 | 3/2002 | Head et al. | |
| 6,376,538 B1 | 4/2002 | Adams | |
| 6,420,418 B1 | 7/2002 | Hagmann et al. | |
| 6,455,550 B1 | 9/2002 | Chen | |
| 6,469,047 B1 | 10/2002 | Jackson et al. | |
| 6,482,849 B1 | 11/2002 | Lobl | |
| 6,489,300 B1 | 12/2002 | Thorsett | |
| 6,521,626 B1 | 2/2003 | Archibald et al. | |
| 6,521,666 B1 | 2/2003 | Sircar | |
| 6,555,562 B1 | 4/2003 | Archibald et al. | |
| 6,645,939 B1 | 11/2003 | Durette et al. | |
| 6,685,617 B1 | 2/2004 | Blinn et al. | |
| 7,026,501 B2 * | 4/2006 | Kawaguchi et al. ........... 560/39 |
| 2003/0166691 A1 | 9/2003 | Archibald et al. | |

FOREIGN PATENT DOCUMENTS

| | | |
|---|---|---|
| DE | 3508251 A1 | 9/1986 |
| EP | 339549 A2 | 11/1989 |
| EP | 0798291 A1 | 10/1997 |
| GB | 2354440 A | 3/2001 |
| JP | 04-275265 A | 9/1992 |
| JP | 09087291 A | 3/1997 |
| JP | 09118662 | 5/1997 |
| WO | WO-95/26360 A1 | 10/1995 |
| WO | WO-97/11960 A1 | 3/1997 |
| WO | WO-97/24342 A1 | 10/1997 |
| WO | WO-97/42216 A1 | 11/1997 |

(Continued)

OTHER PUBLICATIONS

Shieh et al., J. Org. Chem., 1992, vol. 57, pp. 379-381.

(Continued)

*Primary Examiner*—Taylor Victor Oh
(74) *Attorney, Agent, or Firm*—Birch, Stewart, Kolasch & Birch, LLP

(57) ABSTRACT

The present invention provides a process for preparing a novel phenylalanine derivative of the formula (I): wherein X1 is a halogen atom, X2 is a halogen atom, Q is a group of the formula —CH2— or —(CH2)2— and Y is a lower alkyl group, or a pharmaceutically acceptable salt thereof, which has excellent inhibitory effects on α4 integrin-mediated cell adhesion, and an intermediate useful in the process.

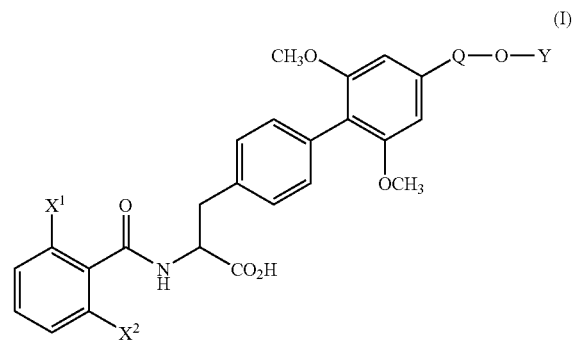

(I)

13 Claims, No Drawings

FOREIGN PATENT DOCUMENTS

| | | |
|---|---|---|
| WO | WO-97/32874 | 12/1997 |
| WO | WO-98/53814 A1 | 12/1998 |
| WO | WO-00/06437 A1 | 2/1999 |
| WO | WO-99/06434 A1 | 2/1999 |
| WO | WO-99/06435 A1 | 2/1999 |
| WO | WO-99/06436 A1 | 2/1999 |
| WO | WO-99/36383 A | 7/1999 |
| WO | WO-99/06390 A1 | 11/1999 |
| WO | WO-99/06431 A1 | 11/1999 |
| WO | WO-99/06432 A1 | 11/1999 |
| WO | WO-99/06433 A1 | 11/1999 |
| WO | WO-99/64390 A1 | 12/1999 |
| WO | WO-99/64395 A1 | 12/1999 |
| WO | WO-00/37429 A2 | 6/2000 |
| WO | WO-00/43372 A1 | 7/2000 |
| WO | WO-02/18320 A | 3/2002 |

OTHER PUBLICATIONS

Sircar et al., Biorganic & Medicinal Chemistry, vol. 10 (2002), pp. 2051-2066.
Satoh et al., Tetrahedron Letters, vol. 38, No. 44, pp. 7645-7648, 1997.
Firooznia, F., et al., Tetrahedron Letters, vol. 39 (1998), pp. 3985-3988.
Firooznia, F., et al., Tetrahedron Letters, vol. 40 (1999), pp. 213-216.
Firoozniz, F., et al., Biorganic & Medicinal Chemistry Letters, vol. 11 (2001) pp. 375-378.
Doherty, G., et al., Biorganic & Medicinal Chemisty Letters, vol. 12 (2002) pp. 729-731.
Doherty, G. et al., Biorganic & Medicinal Chemistry Letters, vol. 12 (2002) pp. 1501-1505.
Yang et al., Biorganic & Medicinal Chemistry Letters, vol. 12 (2002) pp. 1497-1500.
Kamenecka et al., Biorganic & Medicinal Chemistry Letters, vol. 12 (2002) pp. 2205-2208.
Wang et al., Tetrahedron, vol. 58 (2002) pp. 3101-3110.
Gong et al., Organic Letters (2002), vol. 4, No. 22, pp. 3803-3805.
Shroff et al, Biorganic & Medicinal Chemsitry Letters, vol. 6, No. 21, pp. 2495-2500 (1996).
Viney et al., Teh Journal of Immunology, vol. 157, pp. 2488-2497 (1996).
Briskin et al., J. Immunol., vol. 156, pp. 719-726 (1996).
Chemical Abstracts, vol. 65, No. 10, Abstract No. 15302d (1966).
*Barbara Imperiali et al., J. Org. Chem.*, 1993, vol. 58, pp. 1613-1616.
Deprez et al., Biorganic & Medical Chemistry Letters, vol. 6, No. 19, pp. 2317-2322.
I.P. Beletskaya, Journal of Organometallic Chemstry, vol. 250, pp. 551-564 (1983).
The Chemical Society of Japan,"Jikken Kagaku Koza," (Experimental Chemistry), 4th Edition, No. 22, Organic Synthesis IV Acids, Amino Acids, Peptides-, issued by Maruzen K.K., 1992, pp. 138-144.
Sharp, M.J. et al., Tetrahedron Letters, vol. 28, No. 43, pp. 5093-5096 (1987).
Sokolov, S.V. et al, Chemical Abstracts, vol. 65, No. 10, Abstract No. 15302b-e, Nov. 7, 1966.
Shieh et al., J. Org. Chem., 1992, vol. pp. 379-381.
Sircar et al., Biorganic & Medicinal Chemistry, vol. 10 (2002), pp. 2051-2066.
Satoh et al., Tetrahedron Letters, vol. 38, No. 44, pp. 7645-7648, 1997.
Firooznia, F., et al., Tetrahedron Letters, vol. 39 (1998), pp. 3985-3988.
Firooznia, F., et al., Tetrahedron Letters, vol. 40 (1999) pp. 213-216.
Firooznia, F., et al., Biorganic & Medicinal Chemistry Letters, vol. 11 (2001) pp. 375-378.
Doherty, G., et al., Biorganic & Medicinal Chemistry Letters, vol. 12 (2002) pp. 729-731.

* cited by examiner

PROCESS FOR PREPARING A PHENYLALANINE DERIVATIVE AND INTERMEDIATES THEREOF

TECHNICAL FIELD

The present invention relates to a novel process for preparing novel phenylalanine derivatives. The present invention also relates to novel compounds useful as intermediates of the process.

BACKGROUND ART

Integrins participate in various in vivo functions through the binding to adhesion molecules classified into immunoglobulin super family, sialomucin family, and the like. Integrins are composed of subunits referred to as alpha ($\alpha$) and beta ($\beta$) subunits, and there have been identified sixteen $\alpha$ subunits and eight $\beta$ subunits so far. The $\alpha_4$ subunit associates with the $\beta_1$ or $\beta_7$ subunit, and forms $\alpha_4\beta_1$ and $\alpha_4\beta_7$ integrins, respectively, which are hereinafter referred to as "$\alpha_4$ integrin" collectively.

It is known that $\alpha_4$ integrin is involved in various diseases through the adhesion to mucosal addressin cell adhesion molecule-1 (MAdCAM-1), vascular cell adhesion molecule-1 (VCAM-1) or connecting segment 1 (CS-1) on fibronectin. It is also known that when adhesion of $\alpha_4$ integrin is inhibited by an anti-$\alpha_4$ integrin antibody, the symptoms of allergic bronchitis, inflammatory bowel disease, rheumatoid arthritis, experimental autoimmune encephalomyelitis, and the like are alleviated.

It has been reported that there are compounds capable of inhibiting $\alpha_4$ integrin-mediated cell adhesion and that they are useful in treatment of diseases related to $\alpha_4$ integrin-mediated cell adhesion (see, WO 01/12183 and WO99/36393). However, those publications do not disclose compounds having a lower alkoxy-$C_{1-2}$ alkyl group at the 4'-position of biphenylalanine nucleus, and a process for preparing the same.

DISCLOSURE OF INVENTION

One of objects of the present invention is to provide a novel process for preparing a phenylalanine derivative of the formula (I):

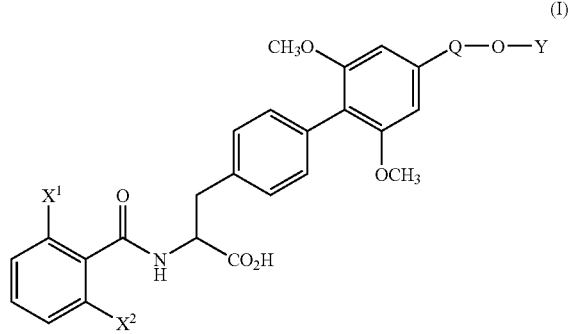

wherein $X^1$ is a halogen atom, $X^2$ is a halogen atom, Q is a group of the formula —CH$_2$— or —(CH$_2$)$_2$— and Y is a lower alkyl group, or a pharmaceutically acceptable salt thereof, which has excellent inhibitory activity against $\alpha_4$ integrin-mediated cell adhesion.

Thus, the present invention relates to a process for preparing a compound of the formula (I):

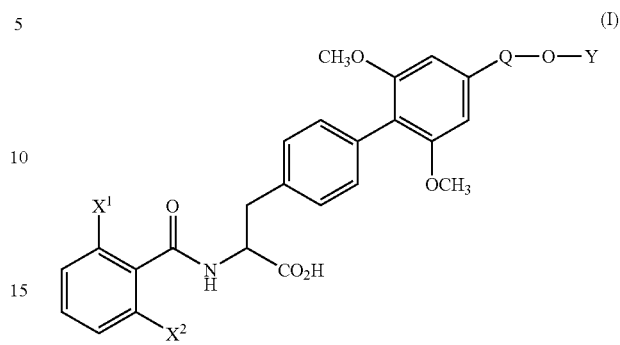

wherein the symbols are the same as defined above, or a pharmaceutically acceptable salt thereof, comprising
(1) coupling a compound of the formula (VI):

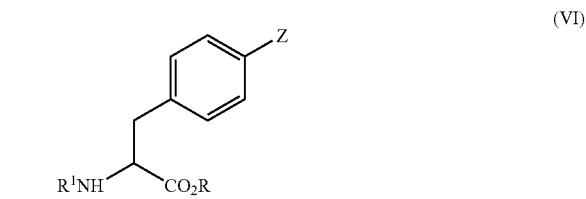

wherein Z is a leaving group, $R^1NH$ is a protected amino group and $CO_2R$ is a protected carboxyl group with a compound of the formula (V):

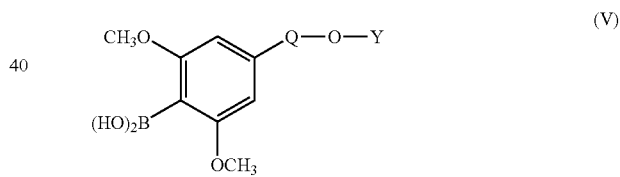

wherein the symbols are the same as defined above, removing the protecting group from the protected amino group, and if necessary, converting the resulting compound into a salt, to yield a compound of the formula (IV):

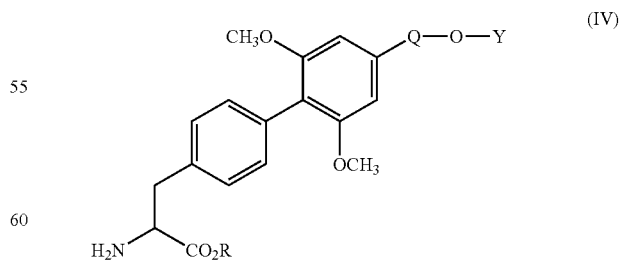

wherein the symbols are the same as defined above, or a salt thereof,
(2) condensing the compound (IV) or a salt thereof with a compound of the formula (III):

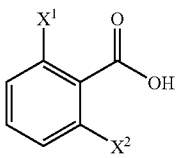

(III)

wherein the symbols are the same as defined above, a salt or a reactive derivative thereof to yield a compound of the formula (II):

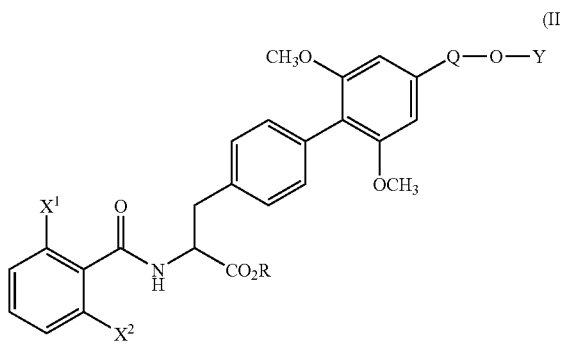

(II)

wherein the symbols are the same as defined above, and
(3) removing the protecting group from the protected carboxyl group of the compound (II), and if necessary, converting the resulting compound into a pharmaceutically acceptable salt.

BEST MODE FOR CARRYING OUT THE INVENTION

The process of the present invention will hereinafter be explained in more detail.

The compounds used in the process of the present invention may be in the form of a salt so long as the reactions are not adversely affected. Examples of the salt include a salt with an inorganic acid such as hydrochloric acid, hydrobromic acid, sulfuric acid, nitric acid or phosphoric acid; a salt with an organic acid such as acetic acid, tartaric acid, citric acid, fumaric acid, maleic acid, toluenesulfonic acid or methanesulfonic acid; a salt with a metal such as sodium, potassium, calcium or alminium; and a salt with a base such as ethylamine, guanidine, ammonium, hydrazine, quinine or cinchonine. When the compounds used in the reactions are available in the free form, they can be converted into a salt in a conventional manner, and vice versa.

(1) STEP 1:

The coupling reaction of compound (VI) with compound (V) can be carried out in a suitable solvent in the presence of a catalyst and a base.

The protecting group for the amino group of compound (VI) can be selected from the amino protecting groups that can be removed easily under conventional conditions. Examples of such amino protecting groups include a substituted or unsubstituted aryl-lower alkoxycarbonyl groups (e.g., benzyloxycarbonyl group and p-nitrobenzyloxycarbonyl group), a lower alkoxycarbonyl group (e.g., t-butoxycarbonyl group), 9-fluorenylmethoxycarbonyl group, etc. Above all, a lower alkoxycarbonyl group is preferred and t-butoxycarbonyl group is most preferred.

Examples of the protected carboxyl group of compound (VI) include esterified carboxyl groups. Specific and preferred examples of the esterified carboxyl groups include carboxyl group esterified with a lower alkyl group, a lower alkenyl group, a lower alkynyl group, an aryl lower alkyl group (e.g., benzyl group), an aryl group (e.g., phenyl group), and the like. Preferred examples of the $CO_2R$ moiety are a lower alkoxycarbonyl group, a lower alkenyloxycarbonyl group, a lower alkynyloxycarbonyl group, an aryl lower alkoxycarbonyl group (e.g., benzyloxycarbonyl group), and an aryloxycarbonyl group (e.g., phenyloxycarbonyl group). Above all, a lower alkoxy-carbonyl group is preferred and ethoxycarbonyl or methoxy-carbonyl group is most preferred.

Examples of the leaving group include a halogen atom (e.g., chlorine atom, bromine atom, iodine atom), an alkanesulfonyloxy group (e.g., methanesulfonyl group) a halogenoalkanesulfonyloxy group (e.g., trifluoromethanesulfonyloxy group) and an arylsulfonyloxy group (e.g., p-toluenesulfonyloxy group). Above all, a halogen atom such as bromine atom and iodine atom, and a halogenoalkanesulfonyloxy group such as trifluoromethanesulfonyloxy group are preferred, and bromine atom and trifluoromethanesulfonyloxy group are most preferred.

The coupling reaction can be carried out under the conditions of Suzuki coupling reaction, making reference to, for example, (a) *Synth. Commun.* 11: 513 (1981); (b) *Pure and Appl. Chem.* 57: 1749 (1985); (c) *Chem. Rev.* 95: 2457 (1995); (d) *J. Org. Chem.* 57: 379 (1992); (e) *Acta Chemica Scandinavica* 47: 221 (1993); (f) *J. Org. Chem.*, 60: 1060 (1995); and (g) *Organic Letters*, 3: 3049 (2001).

Examples of the catalyst include those used in the Suzuki coupling reaction (e.g., palladium or nickel catalysts). Palladium catalysts such as palladium (II) catalysts (e.g., palladium acetate, palladium chloride, dichlorobis(triphenylphosphine)palladium, etc.) and palladium (0) catalysts (palladium tetrakistriphenylphosphine, etc.) can be used conveniently. The palladium catalyst can be used in a catalytic amount, specifically in amount of 1-10 mole %, preferably 4-6 mole %.

In case that a palladium (II) catalyst which does not have ligands in its molecule, such as palladium acetate or palladium chloride, is used, it is preferable to add a phosphine or a phosphite to the reaction in order to facilitate the reaction. Examples of the phosphine include tritolylphosphine, triphenylphosphine, trimethylphosphine, triethylphosphine, etc., and examples of the phosphite include trimethylphosphite, triethylphosphite, tri(n-butyl) phosphite, etc. The phosphine or phosphite can be used in amount of 3-50 mole %, preferably 10-30 mole %.

Among the palladium catalysts above, palladium acetate and palladium chloride are stable and thus preferred, and palladium acetate is more preferred.

Examples of the base that can be used in the reaction include conventional bases, for example, inorganic bases such as alkali metal carbonates (sodium carbonate, potassium carbonate, etc.), alkali metal hydrogen carbonates (sodium hydrogen carbonate, potassium hydrogen carbonate, etc.), alkali metal hydroxides (sodium hydroxide, potassium hydroxide, etc.), and organic bases such as alkylamines (diisopropylamine, triethylamine, diisopropylethylamine, etc.), pyridines (pyridine, dimethylaminopyridine, etc.), and cyclic amines (1,8-diazabicyclo[5.4.0]undec-7-ene, 1,4-diazabicyclo[2.2.2]octane, morpholine, 4-methylmorpholine, etc.). Among them, alkylamines (especially diisopropylamine) and cyclic amines (especially morpholine) are preferred. The base can be conveniently used in an amount of 1.0-3.0 mole equivalents, preferably 1.5-2 mole equivalents.

Any solvents are available so long as the coupling reaction is not adversely affected, and, for example, an organic solvent, water or a mixed solvent thereof can be used. Examples of preferred organic solvent include amides (e.g., dimethylformamide and N-methylpyrrolidone), aromatic hydrocarbons (e.g., benzene and toluene), ethers (e.g., diethyl ether, tetrahydrofuran, dimethoxyethane and dioxane), alcohols (e.g., methanol and ethanol), and a mixture thereof. Above all, amides especially N-methylpyrrolidone is preferred.

The reaction can be carried out at a temperature of −20° C. to 180° C., more preferably at room temperature to 120° C., most preferably at 50° C. to 100° C.

The deprotection method for removing the protecting group from the protected amino group is selected depending on the type of protecting group to be removed. For example, the deprotection can be conducted by a method selected from the followings:

(1) reduction with a catalyst (e.g., palladium on carbon) under a hydrogen atmosphere;
(2) treatment with an acid such as hydrogen chloride, trifluoroacetic acid, p-toluenesulfonic acid, etc.;
(3) treatment with an amine such as piperidine, etc.; and
(4) treatment with a catalyst such as Wilkinson's catalyst, etc., at a temperature of under cooling to under heating in an appropriate solvent selected from organic solvents (e.g., halogenated hydrocarbons such as dichloromethane, chloroform, etc., ethers such as dioxane, tetrahydrofuran, etc., alcohols such as methanol, ethanol, etc., and acetonitrile, etc.), water and a mixed solvent thereof, or without solvent. For example, when the protecting group is t-butoxycarbonyl group, the deprotection can be conducted by acid treatment, specifically, by treatment with a hydrochloric acid or p-toluenesulfonic acid in an appropriate solvent (e.g., esters such as ethyl acetate, etc., or alcohols such as ethanol, etc.) at a temperature of room temperature to under heating, preferably from at 50° C. to the boiling point of the solvent.

(2) STEP 2:

The condensation of the compound (III) or a salt thereof with the compound (IV) or a salt thereof can be carried out using a condensing agent in the presence or absence of a base in an appropriate solvent or without solvent.

The condensing agent can be selected from conventional condensing agents for peptide synthesis, for example, chlorobis(2-oxo-3-oxazolidinyl)phosphine(BOP-Cl), benzotriazol-1-yloxytris(dimethylamino)phosphonium hexafluorophosphate (BOP reagent), dicyclohexylcarbodiimide, 1-(3-dimethylaminopropyl)-3-ethylcarbodiimide hydrochloride (EDC) or carbonyldiimidazole. It is preferred to use an activator such as 1-hydroxybenzotriazole (HOBT) in association with a condensing agent.

Examples of the base that can be used in the reaction include conventional bases, for example, organic bases such as alkylamines (triethylamine, diisopropylethylamine, etc.), pyridines (pyridine, dimethylaminopyridine, etc.) and cyclic amines (1,8-diazabicyclo[5.4.0]undec-7-ene, 4-methylmorpholine, etc.), and inorganic bases such as alkali metal hydroxides (sodium hydroxide, potassium hydroxide, etc.), alkali metal carbonates (sodium carbonate, potassium carbonate, etc.) and alkali metal hydrogen carbonates (sodium hydrogen carbonate, potassium hydrogen carbonate, etc.).

Any solvents are available so long as the condensation reaction is not adversely affected, and, for example, esters (methyl acetate, ethyl acetate, etc.), halogenated hydrocarbons (dichloromethane, chloroform, dichloroethane, carbon tetrachloride, etc.), aromatic hydrocarbons (benzene and toluene), ethers (diethyl ether, tetrahydrofuran, dioxane, etc.), ketones (acetone, methyl ethyl ketone, etc.), amides (dimethylformamide, N-methylpyrrolidone, etc.), or a mixed solvent thereof can be conveniently used.

The reaction can be carried out at a temperature of −50° C. to 50° C., preferably at 0° C. to room temperature.

The condensation reaction of a reactive derivative of compound (III) with a compound (II) or a salt thereof can be carried out in the presence or absence of a base in an appropriate solvent or without solvent.

Examples of the reactive derivative include an acid halide (acid chloride, etc.), a reactive ester (an ester with p-nitrophenol, etc.) and a mixed acid anhydride with other carboxylic acid (a mixed acid anhydride with isobutyric acid, etc.).

Examples of the base that can be used include conventional bases, for example, organic bases such as alkylamines (triethylamine, diisopropylethylamine, etc.), pyridines (pyridine, dimethylaminopyridine, etc.) and cyclic amines (1,8-diazabicyclo[5.4.0]undec-7-ene, 4-methylmorpholine, etc.), and inorganic bases such as alkali metal hydroxides (sodium hydroxide, potassium hydroxide, etc.), alkali metal carbonates (sodium carbonate, potassium carbonate, etc.) and alkali metal hydrogen carbonates (sodium hydrogen carbonate, potassium hydrogen carbonate, etc.).

Any solvents are available so long as the condensation reaction is not adversely affected, and, for example, esters (methyl acetate, ethyl acetate, etc.), halogenated hydrocarbons (dichloromethane, chloroform, dichloroethane, carbon tetrachloride, etc.), aromatic hydrocarbons (benzene, toluene, etc.), ethers (diethyl ether, tetrahydrofuran, dioxane, etc.), ketones (acetone, methyl ethyl ketone, etc.), amides (dimethylformamide, N-methylpyrrolidone, etc.), water, or a mixed solvent thereof can be conveniently used.

It is more preferable to carry out the present condensation reaction under the reaction conditions for so-called Schotten-Baumann reaction among the above-mentioned reaction conditions. For example, the reaction is preferably carried out using an acid halide (preferably, acid chloride) of compound (III) in the presence of an inorganic base such as alkali metal hydrogen carbonate (e.g., sodium hydrogen carbonate, potassium hydrogen carbonate) in a bilayer system of water and an appropriate organic solvent (e.g., ethyl acetate and toluene).

The reaction can be carried out at a temperature of −50° C. to 50° C., preferably at 0° C. to room temperature.

3. STEP (3)

The deprotection method for removing the protecting group from the protected carboxyl group of compound (II) is selected depending on the type of the protecting group to be removed. For example, deprotection can be conducted in a conventional manner such as catalytic reduction, acid treatment, hydrolysis, or the like. In particular, when the protected carboxyl group is an esterified carboxyl group, it can be converted into the carboxyl group by hydrolysis.

Although the hydrolysis may vary depending on the kind of the ester group to be removed, it can be conducted with an acid or a base in a suitable solvent or without solvent. Examples of the acid that can be used include inorganic acids such as hydrochloric acid, nitric acid, sulfuric acid, etc., and organic acids such as trifluoroacetic acid, p-toluenesulfonic acid, etc. Examples of the base that can be used in the reaction include inorganic bases such as alkali metal hydroxides (e.g., lithium hydroxide and sodium hydroxide), alkali metal carbonates (e.g., sodium carbonate and potassium carbonate), alkali metal hydrogen carbonates (e.g., sodium hydrogen carbonate and potassium hydrogen carbonate), alkali earth metal hydroxides (e.g., calcium hydroxide), etc. and organic bases such as alkali metal alkoxides (e.g., sodium methoxide, sodium ethoxide, potassium methoxide and potassium ethoxide), alkali earth metal alkoxides (e.g., calcium methoxide and calcium ethoxide), etc. Alkali metal hydroxides such as lithium hydroxide and sodium hydroxide are preferred. Any solvents are available so long as the hydrolysis is not adversely affected, and, for example, water, an organic solvent or a mixed solvent thereof can be used. Examples of the organic solvent include ethers (e.g., diethyl ether, dioxane and tetrahydrofuran), alcohols (e.g., methanol, ethanol, propanol and ethyleneglycol), acetonitrile and ketones (e.g., acetone and methyl ethyl ketone). Above all, alcohols such as methanol and ethanol and ethers such as dioxane and tetrahydrofuran are preferred.

The reaction can be carried out at a temperature of under cooling to the boiling point of the solvent, preferably at room temperature to 50° C.

The pharmaceutically acceptable salts of the compound (I) include a salt with an inorganic base (e.g., an alkali metal salt such as a sodium salt, a potassium salt, etc.; an alkali earth metal salt such as magnesium salt, calcium salt, etc.) and a salt with an organic base (e.g., ammonium salt; a lower alkyl ammonium salt such as methylammonium salt, ethylammonium salt, etc.; pyridinium salt; or a salt with a basic amino acid such as a salt with lysine, etc.). The compound (I) can be converted into a pharmaceutically acceptable salt in a conventional manner.

Examples of the compounds that are preferably used for carrying out the present process include those wherein $X^1$ is chlorine atom or fluorine atom, $X^2$ is chlorine atom or fluorine atom, Y is a lower alkyl group having 1 to 4 carbon atoms and $CO_2R$ is a lower alkoxycarbonyl group.

More preferred compounds for carrying out the present process include those wherein Q is group of the formula —$CH_2$—, Y is methyl group, ethyl group or n-propyl group, and $CO_2R$ is methqxycarbonyl group, ethoxycarbonyl group or t-butoxycarbonyl group.

Still more preferred compounds for carrying out the present process include those wherein $X^1$ is fluorine atom, Y is methyl group or ethyl group, and $CO_2R$ is methoxycarbonyl group or ethoxycarbonyl group.

Especially preferred compounds for carrying out the present process include those wherein $X^1$ is fluorine atom, $X^2$ is fluorine atom, Y is ethyl group, and $CO_2R$ is ethoxycarbonyl group, or those wherein $X^1$ is fluorine atom, $X^2$ is chlorine atom, Y is ethyl group, and $CO_2R$ is methoxycarbonyl group or ethoxycarbonyl group.

The most preferred compound that can be produced according to the present process is (αS)-α-[(2,6-difluorobenzoyl)amino]-4'-ethoxymethyl-2',6'-dimethoxy(1,1'-biphenyl)-4-propionic acid.

The compound (I) or a pharmaceutically acceptable salt thereof, which is an objective compound of the present process, is a novel compound. The compound (I) or a pharmaceutically acceptable salt thereof not only shows potent inhibitory activity against $α_4$ integrin-mediated cell adhesion but also shows excellent bioavailability after oral administration which reflects overall improvement in metabolic stability, plasma protein binding and aqueous solubility. Accordingly, the compound (I) is useful in treatment of diseases caused by $α_4$ integrin-mediated cell adhesion, including rheumatoid arthritis, atopic dermatitis, psoriasis, asthma, bronchitis, multiple sclerosis, inflammatory bowel disease, experimental autoimmune encephalomyelitis, and the like.

Further, a compound of the formula (IV):

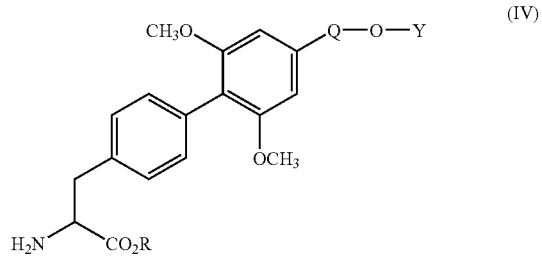

wherein the symbols are the same as defined above, or a salt thereof is novel and useful as an intermediate for the process of the present invention. A compound of the formula (IV) wherein Q is a group of the formula —$CH_2$—, Y is ethyl group, $CO_2R$ is ethoxycarbonyl group, namely, ethyl α-amino-4'-ethoxymethyl-2',6'-dimethoxy(1,1'-biphenyl)-4-propionate or a salt thereof, and especially, in the S-form, is preferred for the process of the present invention.

Besides, another starting compound of the formula (V):

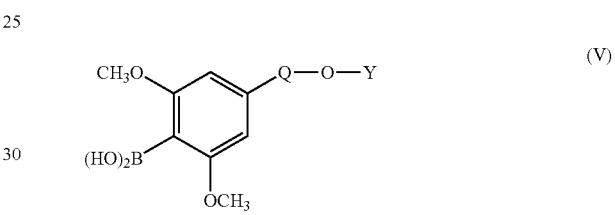

wherein the symbols are the same as defined above is also novel and useful in the reactions for the present process. A compound (V) wherein Q is a group of the formula —$CH_2$— and Y is ethyl group is particularly useful in the present invention.

The compound (V) can be prepared according to the following method.

First, the hydroxyl group of a compound of the formula (VII):

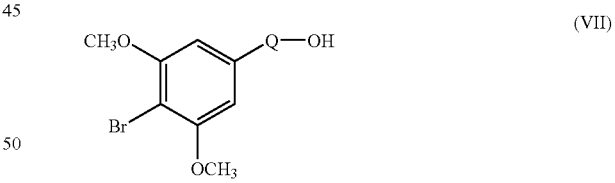

wherein the symbol is the same as defined above, or that of a compound of the formula (VIII):

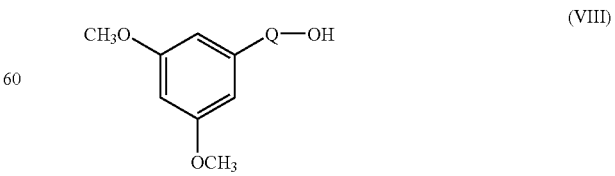

wherein the symbol is the same as defined above is alkylated. The resultant compound is then subjected to lithiation followed by reaction with a tri-lower alkyl borate. The resultant compound is hydrolyzed to give the compound (V).

The alkylation can be carried out using an alkylating agent in a suitable solvent in the presence of a base. Examples of the alkylating agent include di-lower alkyl sulfates such as dimethyl sulfate, diethyl sulfate, etc., and lower alkyl halides such as methyl iodide, ethyl iodide, etc. Examples of the base include inorganic bases such as alkali metal hydroxides (sodium hydroxide, potassium hydroxide, etc.), alkali metal carbonates (sodium carbonate, potassium carbonate, etc.) and alkali metal hydrogen carbonates (sodium hydrogen carbonate, etc.), and organic bases such as alkylamines (triethylamine, diisopropylethylamine, etc.) and pyridines (pyridine, dimethylaminopyridine, etc.). Any solvents are available so long as the reaction is not adversely affected, and, for example, water, acetonitrile, amides (N,N-dimethylformamide, etc.), ethers (tetrahydrofuran, etc.), aromatic hydrocarbons (toluene, etc.), halogenated hydrocarbons (dichloromethane, etc.), or a mixed solvent thereof can be used. The reaction can be carried out in a suitable solvent at a temperature of about 0° C. to about 100° C., preferably at room temperature to about 70° C. The present reaction can be expedited by adding a catalytic amount of a phase-transfer catalyst such as triethylammonium benzyl chloride.

The lithiation and the reaction with tri-lower alkyl borate can be carried out by subjecting a compound to lithiation with an alkyl lithium following by the reaction with a tri-lower alkyl borate in a suitable solvent. Preferred alkyl lithium may be methyl lithium, n-butyl lithium, t-butyl lithium, and the like. Preferred tri-lower alkyl borate may be trimethyl borate, triethyl borate, and the like. Any solvents are available so long as the reaction is not adversely affected, and, for example, organic solvents such as ethers (diethyl ether, tetrahydrofuran, etc.) and a mixed solvent thereof are preferred. The present reaction can be carried out at a temperature of under cooling (e.g., −100° C.) to room temperature.

The hydrolysis can be carried out with an acid in a suitable solvent. Examples of the acid include organic acids such as acetic acid, trifluoroacetic acid and citric acid and inorganic acids such as hydrochloric acid, sulfuric acid and nitric acid. Any solvents are available so long as the reaction is not adversely affected and, for example, organic solvents such as ethers (diethyl ether, tetrahydrofuran, etc.) and a mixed solvent thereof can be used.

Ethyl (αS)-α-[[(1,1-dimethylethoxy)carbonyl]amino]-4-hydroxybenzene propionate and ethyl (αS)-α-[[1,1-dimethylethoxy)carbonyl]amino]-4-(trifluoromethanesulfonyloxy) benzene propionate are described in J. Med. Chem., 33: 1620 (1990) and JP-A-7-157472, respectively. 4-Bromo-3,5-dimethoxybenzyl alcohol is described in, for example, J. Med. Chem., 20: 299 (1977), and can also be prepared according to the following process.

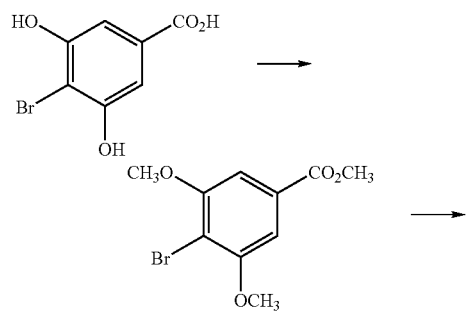

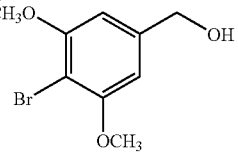

Firstly, 4-bromo-3,5-dihydroxybenzoic acid is methylated to give methyl 4-bromo-3,5-dimethoxybenzoate, which is then reduced to yield 4-bromo-3,5-dimethoxy benzyl alcohol. The methylation can be carried out by reacting with dimethyl sulfate in the presence of a base in a suitable solvent (e.g., ethyl acetate). The reduction can be carried out by reacting with an reducing agent (e.g., lithium alminium hydride, sodium borohydride and calcium borohydride) in a suitable solvent (e.g., tetrahydrofuran).

Throughout the present description and claims, the term "lower alkyl" means straight- or branched-chain alkyl having 1 to 6 carbon atoms, preferably 1 to 4 carbon atoms, for example, methyl, ethyl, propyl, isopropyl, butyl and the like. The term "lower alkoxycarbonyl" means straight- or branched-chain alkoxycarbonyl having 2 to 7 carbon atoms, preferably 2 to 5 carbon atoms, for example, methoxycarbonyl, ethoxycarbonyl, propoxycarbonyl, isopropoxycarbonyl, butoxycarbonyl and the like. The term "lower alkenyl" means straight- or branched-chain alkenyl having 2 to 7 carbon atoms, preferably 2 to 4 carbon atoms, for example, vinyl, allyl, isopropenyl and the like. The term "lower alkenyloxycarbonyl" means straight- or branched-chain alkenyloxycarbonyl having 2 to 7 carbon atoms, preferably 2 to 4 carbon atoms, for example, vinyloxycarbonyl, allyloxycarbonyl, isopropenyloxycarbonyl and the like. The term "lower alkynyl" means straight- or branched-chain alkynyl having 2 to 7 carbon atoms, preferably 2 to 4 carbon atoms, for example, ethynyl, 2-propynyl and the like. The term "lower alkynyloxycarbonyl" means straight- or branched-chain alkynyloxycarbonyl having 2 to 7 carbon atoms, preferably 2 to 4 carbon atoms, for example, ethynyloxycarbonyl, 2-propynyloxycarbonyl and the like. Further, "t-butoxy" means 1,1-dimethylethoxy.

EXAMPLES

The following Examples are provided to further illustrate the process of preparation according to the present invention. In the following examples, some compounds may be referred to by different compound name depending on the nomenclature, as illustrated below.

Ethyl (αS)-α-amino-4'-ethoxymethyl-2',6'-dimethoxy(1,1'-biphenyl)-4-propionate
  Another name: ethyl (2S)-2-amino-3-[4-(4-ethoxymethyl-2,6-dimethoxyphenyl)phenyl]propanoate
Ethyl (αS)-[[1,1-dimethylethoxy]carbonyl]amino]-4'-ethoxymethyl-2',6'-dimethoxy(1,1'-biphenyl)-4-propionate
  Another name 1: ethyl (2S)-2-[(t-butoxycarbonyl)-amino]-3-[4-(4-ethoxymethyl-2,6-dimethoxyphenyl)-phenyl]propanoate
  Another name 2: Ethyl N-(t-butoxycarbonyl)-4-(4-ethoxymethyl-2,6-dimethoxyphenyl)-L-phenylalanine
Ethyl (αS)-α-[(2,6-difluorobenzoyl)amino]-4'-ethoxymethyl-2',6'-dimethoxy(1,1'-biphenyl)-4-propionate
  Another name 1: Ethyl (2S)-2-[(2,6-difluorobenzoyl)amino]-3-[4-(4-ethoxymethyl-2,6-dimethoxyphenyl)phenyl]propanoate Another name 2: Ethyl N-(2,6-difluorobenzoyl)-4-(4-ethoxymethyl-2,6-dimethoxyphenyl)-L-phenylalanine (αS)-α-[(2,6-Difluorobenzoyl)amino]-4'-ethoxymethyl-2',6'-dimethoxy(1,1'-biphenyl)-4-propionic acid Another name 1: (2S)-2-[(2,6-difluorobenzoyl)amino]-3-[4-(4-ethoxymethyl-2,6-dimethoxyphenyl)phenyl]propanoic acid Another name 2: N-(2,6-difluorobenzoyl)-4-(4-ethoxymethyl-2,6-dimethoxyphenyl)-L-phenylalanine

Example 1

(1) Under nitrogen atmosphere, pyridine(130.3 g) and trifluoromethanesulfonic anhydride (170.4 g) were added dropwise to a solution of ethyl (αS)-α-[[(1,1-dimethylethoxy)carbonyl]amino]-4-hydroxybenzenepropionate (170.0 g) in dichloromethane (1.7 L) at 10° C. or below. After stirring for 1 hour at the same temperature, water (850 ml) was added dropwise to the mixture and the mixture was stirred for 2 hours at the same temperature. The organic layer was washed with 10% aqueous citric acid solution and aqueous saturated sodium hydrogen carbonate solution, and dried over magnesium sulfate. The solvent was removed in vacuo to yield ethyl (αS)-α-[[(1,1-dimethylethoxy)carbonyl]amino]-4-(trifluoromethanesulfonyloxy)benzenepropionate (242.5 g) as oil.

MS (m/z): 441 (M$^+$)

(2) Under nitrogen atmosphere, to a mixture of ethyl (αS)-α-[[(1,1-dimethylethoxy)carbonyl]amino]-4-(trifluoromethanesulfonyloxy)benzenepropionate (66.2 g), 4-ethoxymethyl-2,6-dimethoxyphenylboric acid (54.0 g), triphenylphosphine (9.83 g) and N-methylpyrrolidone (330 ml) were added palladium acetate (1.68 g) and diisopropylamine (24.9 g), and the mixture was heated at 90° C. After stirring for 1 hour at the same temperature, the mixture was cooled and toluene and water were added. The organic layers were washed with 10% aqueous citric acid solution and saturated aqueous NaCl solution and dried over magnesium sulfate. The solvent was removed in vacuo to yield ethyl (αS)-α-[[(1,1-dimethylethoxy)carbonyl]amino]-4'-ethoxymethyl-2',6'-dimethoxy(1,1'-biphenyl)-4-propionate (90.1 g) as oil.

The product was dissolved in ethanol (330 ml), and after addition of p-toluenesulfonic acid monohydrate (28.5 g), the mixture was stirred for 2 hours at 75° C. After cooling to room temperature, the mixture was filtrated over charcoal and the filtrate was concentrated under reduced pressure. The residue was dissolved in ethyl acetate with heating. After cooling, the crystalline precipitates were collected by filtration and dried to yield ethyl (αS)-α-amino-4'-ethoxymethyl-2',6'-dimethoxy(1,1'-biphenyl)-4-propionate p-toluenesulfonate (63.4 g).

MS (m/z): 387 (M$^+$-p-toluenesulfonic acid), M.p. 127-129° C.

(3) To a mixture of ethyl (αS)-α-amino-4'-ethoxymethyl-2',6'-dimethoxy(1,1'-biphenyl)-4-propionate p-toluenesulfonate (29.0 g), sodium hydrogen carbonate (15.2 g), water (290 ml) and ethyl acetate (290 ml) was added dropwise 2,6-difluorobenzoyl chloride (9.6 g) at 15° C. or below and the mixture was stirred for 30 minutes at the same temperature. The ethyl acetate layer was washed with saturated aqueous NaCl solution and dried over magnesium sulfate. The solvent was removed in vacuo. The residue was recrystallized from isopropanol-water to yield ethyl (αS)-α-[(2,6-difluorobenzoyl)amino]-4'-ethoxymethyl-2',6'-dimethoxy(1,1'-biphenyl)-4-propionate (26.4 g).

MS (m/z): 527 (M$^+$), M.p. 87-89° C.

(4) To a solution of sodium hydroxide (2.9 g) in water-tetrahydrofuran (317 ml-159 ml) was added ethyl (αS)-α-[(2,6-difluorobenzoyl)amino]-4'-ethoxymethyl-2',6'-dimethoxy(1,1'-biphenyl)-4-propionate (31.7 g) at 15° C. and the mixture was stirred for 4 hours at the same temperature. After neutralizing with 1N HCl, the organic solvent was removed in vacuo. The aqueous layer was cooled, the crystalline precipitates were collected by filtration and recrystallized from ethanol-water to yield (αS)-α-[(2,6-difluorobenzoyl)amino]-4'-ethoxymethyl-2',6'-dimethoxy(1,1'-biphenyl)-4-propionic acid (28.8 g).

MS (m/z): 499 (M$^+$), M.p. 154-155° C.

Example 2

(1) Under nitrogen atmosphere, a mixture of ethyl (αS)-α-[[(1,1-dimethylethoxy)carbonyl]amino]-4-bromobenzene propanoate (11.17 g), 4-ethoxymethyl-2,6-dimethoxyphenylboronic acid (10.80 g), palladium acetate (0.34 g), triphenylphosphine (1.57 g), anhydrous potassium carbonate (12.44 g), N-methylpyrrolidone (56 ml) and water (11 ml) was stirred for 50 minutes at 80° C. After completion of the reaction, the mixture was cooled to room temperature and extracted with ethyl acetate and water. The organic layer was washed with 10% aqueous citric acid solution and saturated aqueous NaCl solution, dried over magnesium sulfate and filtrated. The filtrate was concentrated under reduced pressure to yield ethyl (αS)-α-[[(1,1-dimethylethoxy)carbonyl]amino]-4'-ethoxymethyl-2',6'-dimethoxy(1,1'-biphenyl)-4-propionate (20.4 g) as oil.

The product was dissolved in ethanol (100 ml), and after addition of p-toluenesulfonic acid monohydrate (5.7 g), the mixture was stirred for 1.5 hours at 75° C. After cooling, the mixture was filtrated over charcoal and the filtrate was concentrated under reduced pressure. The residue was suspended in toluene with heating. After cooling, the crystalline precipitates were collected by filtration and dried to yield ethyl (αS)-α-amino-4'-ethoxymethyl-2',6'-dimethoxy(1,1'-biphenyl)-4-propionate p-toluenesulfonate (13.80 g).

(2) The compound obtained in the above step (1) was treated in the same manner as described in Example 1 (2) to (4) to yield (αS)-α-[(2,6-difluorobenzoyl)amino]-4'-ethoxymethyl-2',6'-dimethoxy(1,1'-biphenyl)-4-propionic acid. The physicochemical data were the same as that obtained in Example 1.

Example 3

To a solution of ethyl (αS)-α-[(2,6-difluorobenzoyl)amino]-4'-ethoxymethyl-2',6'-dimethoxy(1,1'-biphenyl)-4-propionate (500 mg) in water (12.6 ml) and dioxane (50 ml) was added hydrochloric acid (12.4 g) and the mixture was stirred for 60 hours at 60° C. The organic solvent was removed in vacuo and the aqueous layer was cooled. The crystalline precipitates were collected by filtration and recrystallized from ethanol-water to yield (αS)-α-[(2,6-difluorobenzoyl)amino]-4'-ethoxymethyl-2',6'-dimethoxy(1,1'-biphenyl)-4-propionic acid (426 mg). The physicochemical data were the same as that obtained in Example 1.

Reference Example 1

(1) To a mixture of 4-bromo-3,5-dimethoxybenzylalcohol (44.5 g), triethylammonium benzyl chloride (2.05 g) and 20% aqueous sodium hydroxide solution (288 g) was added diethyl sulfate (41.7 g) under ice-cooling, and the mixture was stirred overnight at 25-30° C. After stirring for 1 hour at 70° C., the mixture was cooled and extracted with toluene. The toluene layer was washed with water and saturated aqueous NaCl solution and dried over magnesium sulfate. The solvent was removed in vacuo to yield 4-bromo-3,5-dimethoxybenzyl ethyl ether (49.5 g) as colorless oil.

MS (m/z): 276 (M$^+$+2), 274 (M$^+$)

(2) Under nitrogen atmosphere, to a solution of 4-bromo-3,5-dimethoxybenzyl ethyl ether (440.0 g) in tetrahydrofuran (4.0 L) was added dropwise n-butyl lithium (1.6 M n-hexane solution, 1.1 L) at −60° C. After stirring for 15 minutes at the same temperature, trimethyl borate (249.3 g) was added. The temperature of the mixture was gradually elevated, followed by stirring for 1 hour under ice-cooling. To the mixture was added dropwise 10% aqueous sulfuric acid solution (835 g). The mixture was extracted with ethyl acetate and the organic layer was washed with water and saturated aqueous NaCl solution. After drying over magnesium sulfate, the solvent was removed in vacuo. The residue was dissolved in isopropyl ether with heating and cooled. The crystalline precipitates were collected by filtration and dried to yield 4-ethyoxymethyl-2,6-dimetoxyphenylboronic acid (312.9 g).

M.p. 59-61° C.

Reference Example 2

(1) To a suspension of 4-bromo-3,5-dihydroxybenzoic acid (95.0 kg) in ethyl acetate (950 L) were added anhydrous potassium carbonate (270.8 kg) and dimethyl sulfate (174.7 kg). The mixture was heated at 50-80° C. for about 4 hours and partitioned by adding water. The organic layer was washed with water and saturated aqueous NaCl solution and concentrated under reduced pressure. The residue was suspended into methanol, stirred under heating and cooled. The crystalline precipitates were collected by filtration and dried to yield methyl 4-bromo-3,5-dimethoxybenzoate (98.8 kg) as pale yellow crystals.

MS (m/z): 277 (M$^+$+2), 275 (M$^+$), M.p. 120-122° C.

(2) To a solution of calcium chloride (46.5 kg) in ethanol (336 L) were added tetrahydrofuran (672 L) and methyl 4-bromo-3,5-dimethoxybenzoate (96.0 kg) to obtain a suspension. To the suspension was added sodium borohydride (31.7 kg) by portions at room temperature, and the mixture was stirred for about 9 hours at temperature of room temperature to 45° C. The reaction mixture was added dropwise to aqueous HCl solution and stirred for about 16 hours at room temperature. Organic solvent was removed in vacuo, and water (1440 L) was added to the residue and stirred for 1 hour at 50° C. After cooling, the crystalline precipitates were collected by filtration and dried to yield 4-bromo-3,5-dimethoxybenzyl alcohol (83.3 kg) as colorless crystals.

MS (m/z): 249 (M$^+$+2), 247 (M$^+$), M.p. 100-102° C.

INDUSTRIAL APPLICABILITY

The process for preparation of the present invention makes it possible to afford a compound of the formula (I) or a pharmaceutically acceptable salt thereof with high-purity, in a high yield and inexpensively, and, therefore, the process of the present invention is industrially very useful.

What is claimed is:
1. A process for preparing a phenylalanine compound of the formula (I):

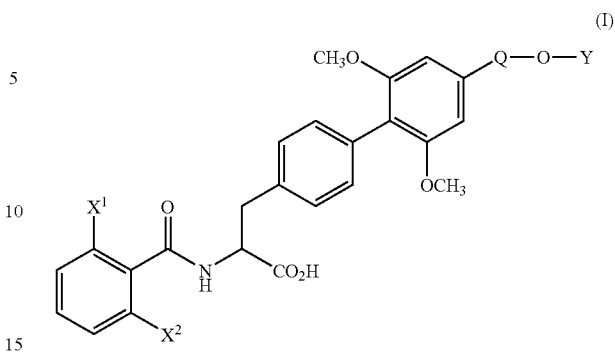

wherein $X^1$ is a halogen atom, $X^2$ is a halogen atom, Q is a group of the formula —$CH_2$— or —$(CH_2)_2$— and Y is a $C_{1-6}$ alkyl group, or a pharmaceutically acceptable salt thereof, which comprises condensing a compound of the formula (IV)

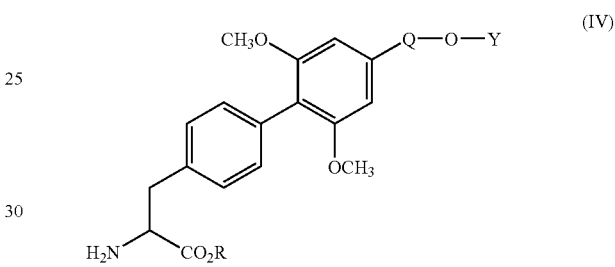

wherein $CO_2R$ is a protected carboxyl group and the other symbols are the same as defined above, or a salt thereof, with a compound of the formula (III):

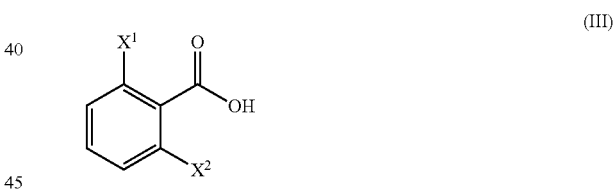

wherein the symbols are the same as defined above, a salt thereof or an acid halide thereof to yield a compound of the formula (II):

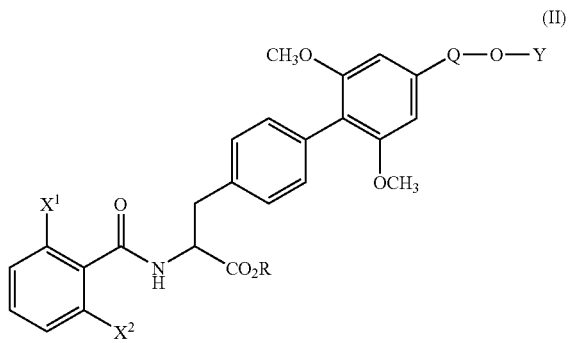

wherein the symbols are the same as defined above, and removing the protecting group from the protected carboxyl group of the compound (II), and, optionally, followed by converting the resulting compound into a pharmaceutically acceptable salt.

2. A process for preparing a phenylalanine compound of the formula (I):

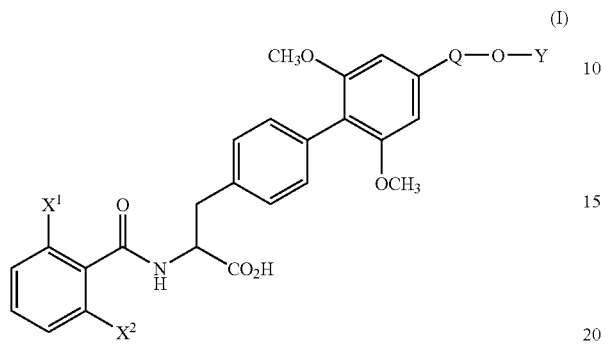

wherein $X^1$ is a halogen atom, $X^2$ is a halogen atom, Q is a group of the formula —$CH_2$— or —$(CH_2)_2$— and Y is a $C_{1-6}$ alkyl group, or a pharmaceutically acceptable salt thereof, which comprises coupling a compound of the formula (VI):

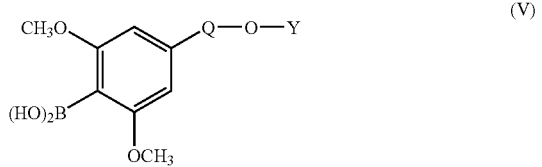

wherein Z is a leaving group, $R^1NH$ is a protected amino group and $CO_2R$ is a protected carboxyl group with a compound of the formula (V):

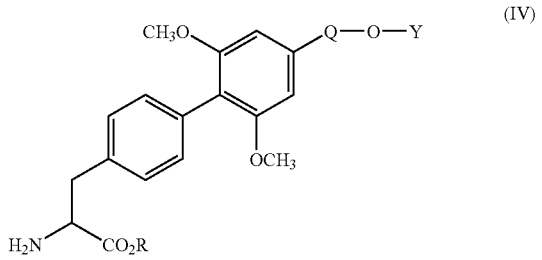

wherein the symbols are the, same as defined above, removing the protecting group from the protected amino group, and, optionally, converting the resulting compound into a salt to yield a compound of the formula (IV):

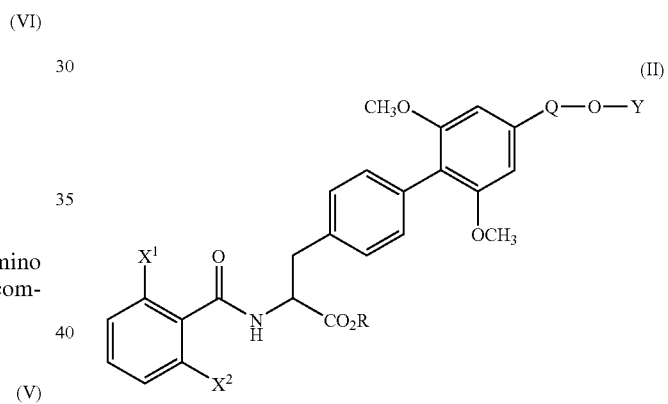

wherein the symbols are the same as defined above, or a salt thereof, and condensing the compound (IV) or a salt thereof with a compound of the formula (III):

wherein the symbols are the same as defined above, a salt thereof or an acid halide thereof to yield a compound of the formula (II):

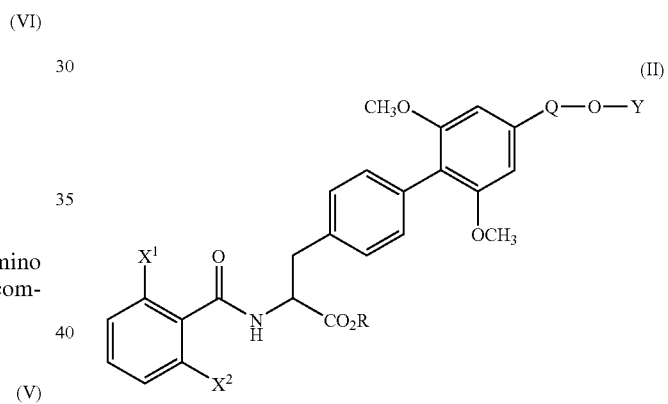

wherein the symbols are the same as defined above, removing the protecting group from the protected carboxyl group of the compound (II), and, optionally followed by converting the resulting compound into a pharmaceutically acceptable salt.

3. The process according to claim 1 or 2, wherein $X^1$ is a chlorine atom or fluorine atom, $X^2$ is a chlorine atom or fluorine atom, Y is a $C_{1-4}$ group and $CO_2R$ is a $C_{2-7}$ alkoxycarbonyl group.

4. The process according to claim 3 wherein Q is a group of the formula —$CH_2$—, Y is a methyl group, ethyl group or n-propyl group, and $CO_2R$ is a methoxycarbonyl group, ethoxycarbonyl group or t-butoxycarbonyl group.

5. The process according to claim 4, wherein $X^1$ is a fluorine atom, Y is a methyl group or ethyl group, and $CO_2R$ is a methoxycarbonyl group or ethoxycarbonyl group.

6. The process according to claim 4, wherein $X^1$ is a fluorine atom, $X^2$ is a fluorine atom, Y is an ethyl group, and $CO_2R$ is an ethoxycarbonyl group.

7. The process according to claim 4, wherein $X^1$ is a fluorine atom, $X^2$ is a chlorine atom, Y is an ethyl group, and $CO_2R$ is a methoxycarbonyl group or an ethoxycarbonyl group.

8. A compound of the formula (IV):

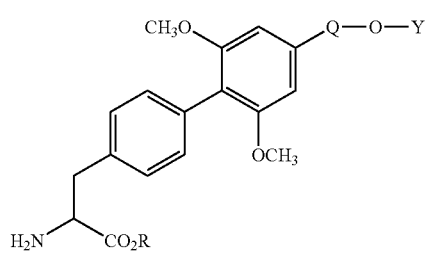
(IV)

wherein Q is a group of the formula —$CH_2$— or —$(CH_2)_2$—, Y is a $C_{1-6}$ alkyl group and $CO_2R$ is a protected carboxyl group, or a salt thereof.

9. The compound according to claim 8, wherein Q is a group of the formula —$CH_2$—, Y is an ethyl group and $CO_2R$ is an ethoxycarbonyl group.

10. A process for preparing a compound of the formula (IV):

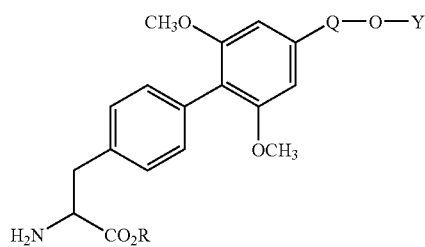
(IV)

wherein Q is a group of the formula —$CH_2$— or —$(CH_2)_2$—, Y is a $C_{1-6}$ alkyl group and $CO_2R$ is a protected carboxyl group, or a salt thereof, which comprises coupling a compound of the formula (VI):

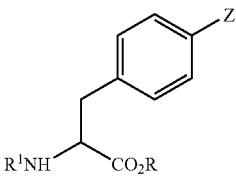
(VI)

wherein Z is a leaving group, $R^1NH$ is a protected amino group and $CO_2R$ is the same as defined above with a compound of the formula (V):

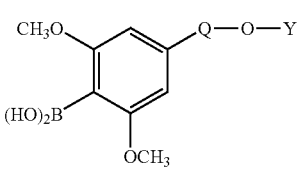
(V)

wherein the symbols are the same as defined above, removing the amino protecting group, and, optionally, followed by converting the resulting compound into a salt.

11. The process according to claim 10, wherein Q is a group of the formula —$CH_2$—, Y is an ethyl group and $CO_2R$ is an ethoxycarbonyl group.

12. A compound of the formula (V):

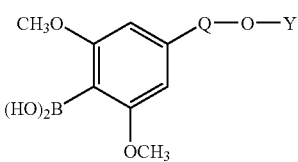
(V)

wherein Q is a group of the formula —$CH_2$— or —$(CH_2)_2$— and Y is a $C_{1-6}$ alkyl group.

13. The compound according to claim 12, wherein Q is a group of the formula —$CH_2$— and Y is an ethyl group.

* * * * *